United States Patent [19]
Rao et al.

[11] Patent Number: 5,902,911
[45] Date of Patent: May 11, 1999

[54] PRODUCTION OF 2-CHLORO-2-HYDROHEXAFLUOROPROPANE AND AZEOTROPES THEREOF WITH HF

[75] Inventors: Velliyur Nott Mallikarjuna Rao; Edwin James Warwas, both of Wilmington, Del.

[73] Assignee: E. I. du Pont de Nemours and Company, Wilmington, Del.

[21] Appl. No.: 08/849,304

[22] PCT Filed: Dec. 1, 1995

[86] PCT No.: PCT/US95/15625

§ 371 Date: Jun. 3, 1997

§ 102(e) Date: Jun. 3, 1997

[87] PCT Pub. No.: WO96/17815

PCT Pub. Date: Jun. 13, 1996

Related U.S. Application Data

[63] Continuation-in-part of application No. 08/351,927, Dec. 8, 1994, Pat. No. 5,481,051.

[51] Int. Cl.⁶ .............................. C07C 19/08; B01D 3/34
[52] U.S. Cl. .............................. 570/134; 203/50; 203/67
[58] Field of Search .................... 570/176, 134; 203/50, 67

[56] References Cited

U.S. PATENT DOCUMENTS

| | | | |
|---|---|---|---|
| 2,942,036 | 6/1960 | Smith et al. | 260/176 |
| 4,319,060 | 3/1982 | Cunningham et al. | 570/177 |
| 4,873,381 | 10/1989 | Kellner et al. | 570/176 |
| 5,036,036 | 7/1991 | Lerou | 502/317 |
| 5,091,600 | 2/1992 | Moore et al. | 570/151 |
| 5,146,018 | 9/1992 | Kellner et al. | 570/176 |
| 5,171,901 | 12/1992 | Gassen et al. | 570/168 |
| 5,463,152 | 10/1995 | Rao | 570/176 |
| 5,481,051 | 1/1996 | Rao | 570/176 |

FOREIGN PATENT DOCUMENTS

| | | |
|---|---|---|
| 0 442 075 | 12/1990 | European Pat. Off. . |
| 0 479 116 | 4/1992 | European Pat. Off. . |
| 1-319441 | 1/1989 | Japan . |
| 1578933 | 5/1977 | United Kingdom . |
| 90 08748 | 8/1990 | WIPO . |
| WO 94/20440 | 9/1994 | WIPO . |
| WO 96/17815 | 6/1996 | WIPO . |

OTHER PUBLICATIONS

Bitner, J.L. et al., Thermochemical and Photochemical studies on organic fluorine compounds, *Chemical Abstract*, 54:22311, 1959.

Zubovich, I.A., Oxidation—Reduction Catalysis by Palladium—Gold and Palladium–Silber Systems on Different Types of Carrier, *Russian Journal of Phys. Chem.*, 56(5), 798–799, 1982.

Sokolskii, D.V. et al., Liquid–phase Hydrogenation of B–Ionone on a Stationary NiCr2O3 Catalyst in a Flow Apparatus under Hydrogeen Pressure, *Russian Journal of Phys. Chem.*, 56(7), 1075–1076, 1982.

*Primary Examiner*—Alan Siegel

[57] ABSTRACT

A process is disclosed for the monohydrogenolysis of 2,2-dichlorohexafluoropropane to 2-chloro-2-hydrohexafluoropropane. The process involves reacting the 2,2-dichlorohexafluoropropane with hydrogen at an elevated temperature of about 150° C. or less in the presence of a catalyst containing a catalytically effective amount of palladium supported on trivalent chromium oxide in the presence of an acid of the formula HZ (where Z is Cl and/or F) to produce 2-chloro-2-hydrohexafluoropropane with a selectivity of over 70% based upon the 2,2-dichlorohexafluoropropane converted. Azeotropes of 2-chloro-2-hydrohexafluoropropane with HF are also disclosed; as are processes for producing such azeotropes.

5 Claims, No Drawings

PRODUCTION OF 2-CHLORO-2-HYDROHEXAFLUOROPROPANE AND AZEOTROPES THEREOF WITH HF

RELATED APPLICATION

This application is national filing under 35 USC 37 of International Application No. PCT/US95/15625, which is a continuation-in-part of pending U.S. patent application Ser. No. 08/351,927 filed Dec. 8, 1994, which issued as U.S. Pat. No. 5,481,051.

FIELD OF THE INVENTION

This invention relates to the production of hydrohalofluorocarbons and their azeotropes with HF, and more particularly to the hydrogenolysis reactions of 2,2-dichlorohexafluoropropane using palladium-containing catalysts and products which can be produced thereby.

BACKGROUND

Various processes for the catalytic hydrogenolysis of chlorofluorocarbons and hydrochlorofluorocarbons are known. For example, U.S. Pat. No. 2,942,036 discloses the reaction of 1,2,2-trichloropentafluoropropane with hydrogen in the presence of palladium on activated carbon catalyst to produce 1,2,2-trihydropentafluoropropane. The examples show that under the conditions of the experiments one of the products from this reaction is $CF_3CH=CF_2$. Japanese Patent Application Publication Hei 1(1989)-319441 discloses a process where one chlorine atom is selectively replaced by hydrogen in 1,1,1-trichlorotrifluoroethane using a platinum catalyst. For comparison, a palladium on carbon catalyst is disclosed to produce 1,1,1-trifluoroethane as the major product under the conditions of the experiment.

It is well known that the hydrogenolysis of compounds such as chlorofluorocarbons to replace chlorine by hydrogen produces hydrogen chloride as a co-product. Loss of fluorine when it occurs (e.g., to produce overhydrogenated products) can produce HF as a by-product.

SUMMARY OF THE INVENTION

The present invention provides a process for the monohydrogenolysis of 2,2-dichlorohexafluoropropane (i.e., $CF_3CCl_2CF_3$, or CFC-216aa) to 2-chloro-2-hydrohexafluoropropane (i.e., $CF_3CHClCF_3$, or HCFC-226da). The process comprises reacting said 2,2-dichlorohexafluoropropane with hydrogen at an elevated temperature of about 150° C. or less in the presence of a catalyst containing a catalytically effective amount of palladium supported on trivalent chromium oxide in the presence of an acid of the formula HZ, where Z is selected from the group consisting of Cl, F and mixtures thereof, to produce 2-chloro-2-hydrohexafluoropropane with a selectivity of over 70% based upon the 2,2-dichlorohexafluoropropane converted.

Azeotropic compositions (e.g., an azeotropic composition comprising from about 80 to 47 mole percent HF and from about 20 to 53 mole percent $CF_3CHClCF_3$) are also provided; as is a process for producing an azeotropic composition of HF and 2-chloro-2-hydrohexafluoropropane as a product of the monohydrogenolysis of 2,2-dichlorohexafluoropropane where HF is present.

DETAILED DESCRIPTION

The catalysts suitable for the process of this invention comprise palladium and may optionally contain other components such as other Group VIII metals. The palladium is supported on chromium oxide. Any source of chromium oxide is suitable, but chromium oxide prepared by the thermal decomposition of $(NH_4)_2Cr_2O_7$ is especially preferred. A procedure for the preparation of $Cr_2O_3$ by the thermal decomposition of $(NH_4)_2Cr_2O_7$ is disclosed in U.S. Pat. No. 5,036,036, the entire contents of which are incorporated herein by reference.

The acid HZ is at least partially produced during the reaction as the halogen Cl is removed from the starting material as a result of the hydrogenolysis. Accordingly, Z is ordinarily at least in part Cl. Also of note are embodiments where Z is partially F (i.e., the acid is a mixture of HCl and HF). HF can be present for example, as a result of overhydrogenolysis, wherein fluorine substituents of the starting material are partially replaced by hydrogen. HF can also be present in the reaction feed. For example, residual HF can be present from processes used to make the 2,2-dichlorohexafluoropropane. Of note in this regard are embodiments where said starting material is a component of an azeotrope of HF and said starting material, and starting material from said azeotrope is reacted with hydrogen in the presence of HF from said azeotrope.

Unlike alumina supports which are readily fluorinated, chromia fluorinates much more slowly under the same reaction conditions. Without wishing to be bound by theory, it is believed that because of the slower fluorination, chromia supports maintain their surface area longer than alumina supports; thereby enhancing catalyst life.

The palladium-containing material used to prepare the catalyst is preferably from a palladium salt (e.g., palladium chloride). The other metals which may be added to the catalyst include those from Group VIII (e.g., Pt, Rh, Ru or Ni). The metal may be added in the conventional manner (e.g., as a soluble salt of the metal). The concentration of palladium supported on the chromium oxide support is typically within the range from about 0.2% to about 5% by weight of the catalyst. The concentration of other Group VIII metals, when present, is typically within the range of from 0% to about 3% by weight of the catalyst, but palladium is ordinarily at least 60% by weight of the total supported metal, (preferably, at least 80% of the total supported metal).

The hydrogenolysis of the present invention is conducted at an elevated temperature. Ordinarily the temperature is about 150° C. or less. Typically satisfactory reaction rates are achieved at operating temperatures of about 100 to 125° C. Generally, in order to provide substantial hydrogenolysis product yields, the amount of hydrogen used is at least about 0.5 mole per mole of the organic starting material. To provide yields desired in many embodiments, at least stoichiometric amounts of hydrogen are used. A considerable excess of hydrogen can also be advantageously employed to provide the yields desired in many embodiments in addition to serving as a heat sink to reduce the overall temperature rise in the reactor. The amount of the monohydrogenolysis product in the reaction product mixture containing the same number of fluorines as the starting material is typically at least 70%.

The process of this invention is especially suitable for the production of 2-chloro-2-hydrohexafluoropropane (HCFC-226da) from 2,2-dichlorohexafluoropropane (CFC-216aa). The monohydrogenolysis product, HCFC-226da is a valuable intermediate for the synthesis of other fluorine containing materials, such as $CF_3CHFCF_3$ (HFC-227ea) which is useful as a fire extinguishant.

Pressure is not critical. Atmospheric and superatmospheric pressures are the most convenient and are therefore preferred.

The reaction products may be separated by conventional techniques, such as distillation. Hydrochlorofluorocarbons such as 2-chloro-2-hydrohexafluoropropane (HCFC-226da) likely form azeotropes with HF; and conventional decantation/distillation may be employed if further purification of HCFC-226da is desired. An azeotrope is a liquid mixture that exhibits a maximum or minimum boiling point relative to the boiling points of surrounding mixture compositions. A characteristic of minimum boiling azeotropes is that the bulk liquid composition is the same as the vapor compositions in equilibrium therewith, and distillation is ineffective as a separation technique. It has been found, for example, that $CF_3CHClCF_3$ (HCFC-226da) and HF form a minimum boiling azeotrope. This azeotrope can be produced as a co-product with HCFC-226da. As discussed further below, compositions may be formed which consist essentially of azeotropic combinations of hydrogen fluoride with HCFC-226da. These include a composition consisting essentially of from about 47 to 80 mole percent HF and from about 53 to 20 mole percent HCFC-226da (which forms an azeotrope boiling at a temperature between −50° C. and about 130° C. at a pressure between about 7.2 kPa and about 4391 kPa). The hydrochlorofluorocarbons (e.g., HCFC-226da) can be separated from the HF in such azeotropes by conventional means such as neutralization and decantation. However, azeotropic compositions of the hydrochlorofluorocarbons and HF (e.g., an azeotrope recovered by distillation of hydrogenolysis reactor effluent) are useful as recycle to a fluorination reactor, where the recycled HF and the recycled hydrochlorofluorocarbon can function as reactants. Thus, for example, the process of this invention for producing $CF_3CHClCF_3$ by the reaction of $CF_3CCl_2CF_3$ with $H_2$ in the presence of HF can further comprise the steps of recovering a portion of the $CF_3CClHCF_3$ as an azeotropic composition of $CF_3CClHCF_3$ and HF; and can be followed by a process for producing $CF_3CHFCF_3$ which comprises recycling said azeotropic composition to a fluorination reactor where $CF_3CClHCF_3$ is reacted with HF. $CF_3CHFCF_3$ is useful as a fire extinguishant.

HCFC-226da/HF Azeotrope

As noted above, the present invention provides a composition which consists essentially of hydrogen fluoride and an effective amount of a $CF_3CHClCF_3$ to form an azeotropic combination with hydrogen fluoride. By effective amount is meant an amount which, when combined with HF, results in the formation of an azeotrope or azeotrope-like mixture. As recognized in the art, an azeotrope or an azeotrope-like composition is an admixture of two or more different components which, when in liquid form under given pressure, will boil at a substantially constant temperature, which temperature ay be higher or lower than the boiling temperatures of the individual components, and which will provide a vapor composition essentially identical to the liquid composition undergoing boiling.

For the purpose of this discussion, azeotrope-like composition means a composition which behaves like an azeotrope (i.e., has constant-boiling characteristics or a tendency not to fractionate upon boiling or evaporation). Thus, the composition of the vapor formed during boiling or evaporation of such compositions is the same as or substantially the same as the original liquid composition. Hence, during boiling or evaporation, the liquid composition, if it changes at all, changes only to a minimal or negligible extent. This is to be contrasted with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotropic composition may change when the azeotrope or azeotrope-like liquid composition is subjected to boiling at different pressures. Thus an azeotrope or an azeotrope-like composition may be defined in terms of the unique relationship that exists among components or in terms of the compositional ranges of the components or in terms of exact weight percentages of each component of the composition characterized by a fixed boiling point at a specified pressure. It is also recognized in the art that various azeotropic compositions (including their boiling points at particular pressures) may be calculated (see, e.g., W. Schotte, Ind. Eng. Chem. Process Des. Dev. 1980, 19, pp 432–439). Experimental identification of azeotropic compositions involving the same components may be used to confirm the accuracy of such calculations and/or to modify the calculations for azeotropic compositions at the same or other temperatures and pressures.

It has been found that azeotropes of HF and HCFC-226da are formed at a variety of temperatures and pressures. At a pressure of 30.47 psia (210 kPa) and 20° C., the azeotrope vapor composition was found to be about 69.5 mole percent HF and about 30.5 mole percent HCFC-226da. Based upon the above findings, it has been calculated that an azeotropic composition of about 79.7 mole percent HF and about 20.3 mole percent HCFC-226da can be formed at −50° C. and 1.04 psia (7.2 kPa) and an azeotropic composition of about 47.4 mole percent HF and about 52.6 mole percent HCFC-226da can be formed at 130° C. and 637 psia (4391 kPa). Accordingly, the present invention provides an azeotrope or azeotrope-like composition consisting essentially of from about 80 to 47 mole percent HF and from about 20 to 53 mole percent HCFC-226da, said composition having a boiling point from about −50° C. at 7.2 kPa to about 130° C. at 4391 kPa.

Practice of the invention will become further apparent from the following non-limiting examples.

EXAMPLE

Catalyst Preparation

A solution containing palladium chloride (2.88 g), conc. hydrochloric acid (3 mL) and deionized water (100 mL) was prepared in a round-bottom flask. To this solution was added chromium oxide, $Cr_2O_3$, (98 g, 10×20 mesh (1.7×0.83 mm)) prepared by the pyrolysis of $(NH_4)_2Cr_2O_7$. The resulting slurry was stirred frequently and then dried in air at 150° C. for about 18 hours; followed by calcination in air for about 8 hours. Palladium on chromium oxide (96.7 g), containing about 2% palladium was isolated.

Hydrogenolysis of CFC-216aa using Palladium on Chromium Oxide catalyst

Liquid CFC-216aa ($CF_3CCl_2CF_3$), 3 mL/hour was vaporized and mixed with 20 cc/minute of hydrogen. This vapor mixture was sent through a 0.5" (1.3 mm) O.D.×8" (203 mm) Hastelloy™ nickel alloy reactor containing 19.2 g of 10×20 mesh (1.7 mm×0.83 mm) palladium on chromium oxide catalyst (2 weight percent palladium) heated in a fluidized sand bath maintained at 100° C. The catalyst was heated at 400° C. in a stream of hydrogen fluoride for about 30 minutes and subsequently reduced in a stream of hydrogen at about 150° C. for about two hours prior to use (at 100° C.) for the hydrogenolysis. Organic product analysis using conventional gas chromatography after the catalyst was in use for about twenty hours of operation showed that CFC-216aa conversion was about 92%. The hydrogen-containing products included 4.0% HFC-236fa ($CF_3CH_2CF_3$), 86.0% HCFC-226da ($CF_3CHClCF_3$) and small amounts of other products. Only a small portion of the total reactor effluent was sent to the gas chromatograph for organic product analysis. The bulk of the product stream which also contains inorganic acids such as HCl and HF was sent to a caustic scrubber for neutralization of the acids.

The above reaction was repeated except that the reaction temperature was 150° C. CFC-216aa conversion was essentially complete. The hydrogen-containing products included about 9.5% HFC-236fa and 83% HCFC-226da and small amounts of other products.

The above reaction was repeated except that the reaction temperature was 200° C. Again, CFC-216aa conversion was essentially complete. In addition to the hydrogen-containing products, HFC-236fa (23%) and HCFC-226da (62%), there was about 10% propane in addition to other minor by-products.

Comparative Example

Hydrogenolysis of CFC-216aa

Using Palladium on Low-Ash Acid-Washed Carbon Carbon Support

The carbon support used in the examples was a 4×8 mesh (about 4.7 mm×2.4 mm) commercial grade coconut shell carbon which had (before washing) an ash content of about 2.6 weight percent. After hydrochloric acid washing, the carbon support had an ash content of less than about 0.1 weight percent.

Liquid CFC-216aa, 3 mL/hour, was vaporized and mixed with 10 cc/minute of hydrogen. This vapor mixture was sent through a 0.5" (12.7 mm) O.D.×8" (203 mm) Hastelloy™ nickel alloy reactor containing 7.2 g of 0.5 weight percent palladium supported on acid-washed carbon maintained at 150° C. using a fluidized sand bath. Only a small portion of the total reactor effluent was sent to the gas chromatograph for organic product analysis. The bulk of the product stream which also contains inorganic acids such as HCl and HF was sent to a caustic scrubber for neutralization of the acids. Organic product analysis using conventional gas chromatography indicated that about 90% of the starting material had been converted. The hydrogen-containing products included 15.7% 2,2-dihydrohexafluoropropane (HFC-236fa), 54.3% 2-chloro-2-hydrohexafluoropropane (HCFC-226da), 12.3% 2-hydropentafluoropropene, and 1.7% 1,2,2-trihydropentafluoropropane (HFC-235fa) and small quantities of other compounds.

This example was repeated except that the hydrogen flowrate was increased to 30 cc/minute. Organic product analysis using conventional gas chromatography indicated that the starting material conversion was essentially complete. The hydrogen-containing products included 24.8% 2,2-dihydrohexafluoropropane (HFC-236fa), 54.6% 2-chloro-2-hydrohexafluoropropane (HCFC-226da) and 19.8% 1,2,2-trihydropentafluoropropane (HFC-235fa) and small quantities of other compounds.

This comparative experiment illustrates that when using palladium supported on acid-washed carbon as catalyst for the hydrogenolysis of CFC-216aa (where two chlorines of the starting compound are on the middle carbon and the two adjacent carbons contain trifluoromethyl groups) an olefin and/or a saturated product containing one less fluorine than the starting compound can be produced in significant amounts.

What is claimed is:

1. An azeotropic composition consisting essentially of from about 80 to 47 mole percent HF and from about 20 to 53 mole percent $CF_3CHClCF_3$, which forms an azeotrope boiling at a temperature between about −50° C. and 130° C. at a pressure between about 7.2 kPa and 4391 kPa.

2. The azeotrope composition of claim 1 produced by a process comprising the steps of reacting 2,2-dichlorohexafluoropropane with hydrogen at an elevated temperature of about 150° C. or less in the presence of a catalyst containing a catalytically effective amount of palladium supported on trivalent chromium oxide in the presence of HF to produce 2-chloro-2-hydrohexafluoropropane with a selectivity of over 70% based upon the 2,2-dichlorohexafluoropropane converted; and recovering a portion of the $CF_3CHClCF_3$ as an azeotropic composition of $CF_3CHClCF_3$ and HF.

3. The azeotropic composition of claim 1 which consists essentially of about 69.5 mole percent HF and about 30.5 mole percent $CF_3CHClCF_3$, which forms an azeotrope boiling at a temperature of about 20° C. and a pressure of about 210 kPa.

4. The azeotrope composition of claim 3 produced by a process comprising the steps of reacting 2,2-dichlorohexafluoropropane with hydrogen at an elevated temperature of about 150° C. or less in the presence of a catalyst containing a catalytically effective amount of palladium supported on trivalent chromium oxide in the presence of HF to produce 2-chloro-2-hydrohexafluoropropane with a selectivity of over 70% based upon the 2,2-dichlorohexafluoropropane converted; and recovering a portion of the $CF_3CHClCF_3$ as an azeotropic composition of $CF_3CHClCF_3$ and HF.

5. An azeotropic composition of 2-chloro-2hydrohexafluoropropane and HF produced by a process comprising the steps of reacting 2,2-dichlorohexafluoropropane with hydrogen at an elevated temperature of about 150° C. or less in the presence of a catalyst containing a catalytically effective amount of palladium supported on trivalent chromium oxide in the presence of HF to produce 2-chloro-2-hydrohexafluoropropane with a selectivity of over 70% based upon the 2,2-dichlorohexafluoropropane converted; and recovering a portion of the $CF_3CHClCF_3$ as an azeotropic composition of $CF_3CHClCF_3$ and HF.

* * * * *